US00PP33652P2

(12) United States Plant Patent
Hansen

(10) Patent No.: US PP33,652 P2
(45) Date of Patent: Nov. 16, 2021

(54) ***SALVIA* PLANT NAMED 'WHITE PROFUSION'**

(50) Latin Name: ***Salvia nemorosa* (Linnaeus)**
Varietal Denomination: White Profusion

(71) Applicant: Hans A Hansen, Zeeland, MI (US)

(72) Inventor: Hans A Hansen, Zeeland, MI (US)

(73) Assignee: Waters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,730

(22) Filed: Nov. 26, 2019

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508
See application file for complete search history.

*Primary Examiner* — Anne Marie Grunberg

(57) ABSTRACT

A new and distinct cultivar of perennial *Salvia* plant named 'White Profusion' characterized by pure, clean, white flowers beginning late spring and continuing through late summer if deadheaded with densely arranged in verticils with light green-colored calyces. The new plant has a compact habit with stiff, upright, heavily-branched stems with very strong tendency to repeat when deadheaded, a strong vigorous growth rate and rugose gray-green foliage. It is useful for landscaping specimens, en masse or as a container plant.

1 Drawing Sheet

Botanical denomination: *Salvia nemorosa* (Linnaeus).
Cultivar designation: 'White Profusion'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 8, 2019. Prior to that, on Dec. 1, 2018 the claimed plant was displayed with a photograph and brief description in a website operated by Walters Gardens, Inc., and on May 29, 2019 the new plant was promoted in the "Walters Gardens 19-20 Catalog". Walters Gardens, Inc. obtained the new plant and all information relating thereto, from the inventor. No plants of *Salvia* 'White Profusion' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'White Profusion' or as the new plant. The new plant was selected from a cross between the female parent, an unreleased proprietary hybrid known only by the breeder code 12-60-3 (not patented) and an unknown male on Jun. 11, 2014 at a wholesale perennial nursery in Zeeland, Mich. Seeds were collected in the summer of 2014 and the new plant begun the trial phase in the summer of 2016 and eventually assigned the breeder code 14-27-2 prior to assigning a cultivar name.

The new *Salvia* was further evaluated and asexually propagated first by division in 2016 and propagated by basal cuttings taken at the same nursery in Zeeland, Mich., USA in July of 2017. Evaluation of these and further cutting grown plants shows that *Salvia* 'White Profusion' continues to be stable and produce true to type plants in successive generations of asexual propagation.

SUMMARY OF THE INVENTION

Plants of *Salvia* 'White Profusion' can be most closely compared to *Salvia* 'Bumblesnow' U.S. Plant Pat. No. 31,399, 'Snowhill' ('Schneehuegel') (not patented) and 'Sensation White' (not patented). 'Bumblesnow' U.S. Plant Pat. No. 31,399 is shorter and more compact with slightly less reblooming potential. 'Snow Hill' ('Schneehugel') (not patented) is taller and looser in habit. 'Sensation White' is shorter with less dense flowering. 'White Profusion' has better repeat flowering than all of the above comparison cultivars. The female parent has blue flowers and taller in habit.

The following characteristics in combination distinguish *Salvia* 'White Profusion' as a new and distinct cultivar from all other cultivars known to the inventor:

1. Pure, clean, white flowers densely arranged in dense verticils;
2. Stiff, upright, heavily-branched, dense, flower stems;
3. Very strong repeat flowering when deadheaded;
4. Compact, rounded, strong, vigorous and winter-hardy habit;
5. Rugose gray-green foliage;
6. Calyces of light green.

BRIEF DESCRIPTION OF THE DRAWINGS

The photographs of the new plant demonstrate the unique traits and the overall appearance of *Salvia* 'White Profusion'. The colors are as accurate as reasonably possible with color reproductions. Variation in ambient light spectrum, source and direction may cause the appearance of minor variation in color. The plant used in the photographs was a three-year-old plant grown in an open, full-sun trial garden at a wholesale perennial nursery in Zeeland, Mich. with supplemental water and fertilizer when needed.

DETAILED BOTANICAL DESCRIPTION

Figure 1:
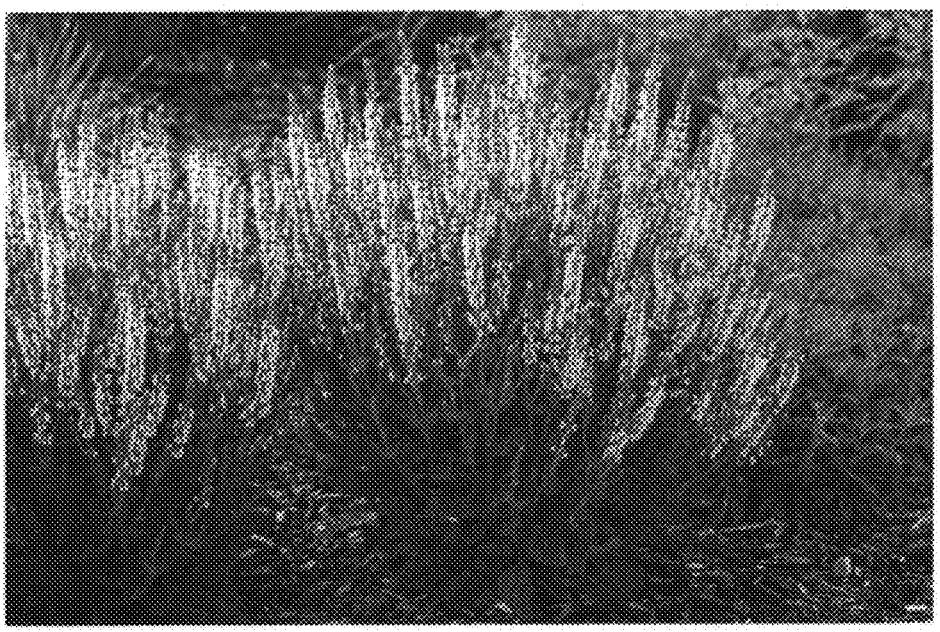
FIG. 1 shows the plant habit in full flower in a landscape.
Figure 2:
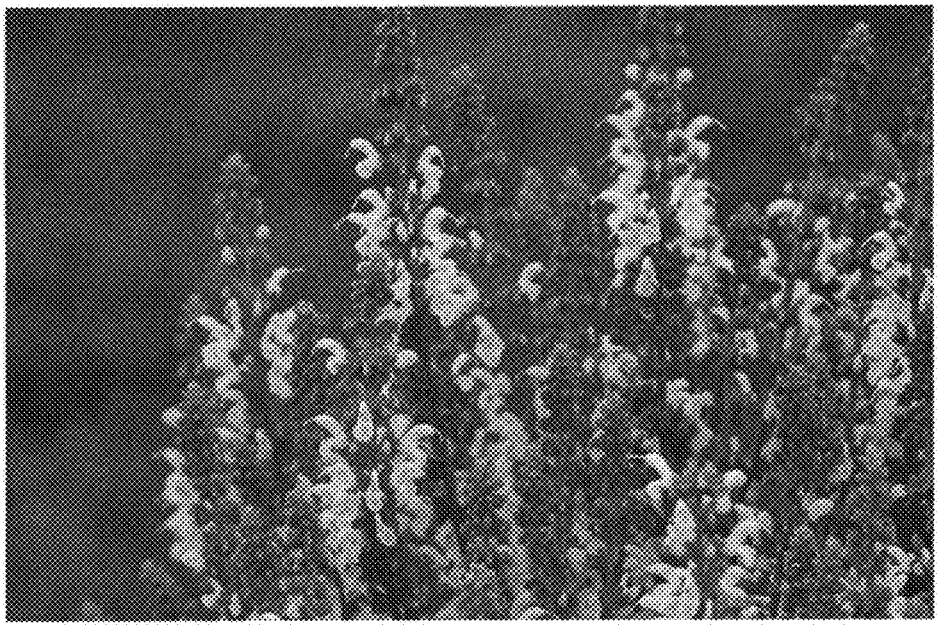
FIG. 2 shows a close-up of the flower scapes with the buds, flowers, stems and calyxes.

The following descriptions and color references except where common dictionary terms are used are based on the 2015 edition of The Royal Horticultural Society Colour Chart. *Salvia* 'White Profusion' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in an outdoor full-sun trial garden and in a greenhouse at a wholesale perennial nursery in Zeeland, Mich. and greenhouse forced two-year-old plants. Plants were given supplemental water and fertilizer.

Botanical classification: *Salvia nemorosa* (Linnaeus);

Parentage: Female or seed parent the unreleased hybrid 12-60-3; the male or pollen parent is unknown;

Plant habit: Winter-hardy herbaceous perennial; multi-stemmed, compact, rounded, with basal and cauline foliage, and flowers in several, tightly-arranged verticils on dense, highly-branched, upright racemes displayed above foliage; flowering to about 47.0 cm tall and about 50.0 cm wide at the fullest point about 20 cm above soil; with cauline foliage below branches;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks;

Root description: Fine, well-branched; color dependent on age and soil type, from cream to dark tan in color; typically nearest RHS 161D;

Foliage: Opposite, simple, rugose, lanceolate; margin bi-crenulate; glabrous and matte abaxial and adaxial surfaces; acute apex and base cordate to truncate; leaf blades about 8.5 cm long and 3.5 cm across, decreasing in size distally; average about 6.0 cm long and 2.3 cm across; faint sage fragrance; leaf variegation absent;

Foliage color: Adaxial surface between RHS NN137C and RHS 137A; abaxial surface nearest RHS 147B;

Venation: Reticulate; impressed on adaxial side and costate on abaxial side; abaxial midrib puberulent secondary veins glabrous; adaxial puberulent;

Vein color: Adaxial midrib between RHS 146D and RHS 145D, secondary veins nearest RHS 148D; abaxial midrib nearest RHS 145D and primary and secondary veins nearest RHS 148D;

Petiole: Concavo-convex; puberulent adaxial and abaxial and ciliolate margin distally and ciliate proximally; to about 3.5 cm long and 5.0 mm wide, average 3.0 cm long and 4.0 mm wide at base;

Petiole color: Adaxial and abaxial surfaces nearest 145B in center with margin nearest RHS 138A;

Inflorescence description: Perfect, bilabiate, verticillate with flowering generally beginning at lower verticils and advancing up the scape, but not all flowers at each verticil opening at the same time giving the effect of a scape being in continuous flower for longer periods; average distance between verticils about 1.5 mm, greater proximally and less distally; self-cleaning, petals not persistent; flowering beginning late spring for about six weeks and repeating though late summer if scapes removed after flowering; total length about 43 cm long, flowering in upper 15 cm and branching to about 7 cm wide; average internode distance about 6 mm; number of flowers per node or verticil about 12 in lowest nodes, decreasing distally;

Inflorescence attitude: With midline projected about 30 degree angle above horizontal, hood petal about 55 degree angle above horizontal and lower lip about 20 degrees above horizontal;

Flower longevity: About four days on the plant or as cut flower;

Fragrance: None detected under present growing conditions;

Flower buds one day prior to anthesis: Shape is rounded on top and slightly concave below, with rounded apex; micro-puberulent; about 9.0 mm long, 3.0 mm tall and 2.0 mm wide;

Bud color: Exposed dorsal petal nearest RHS 157D, ventral petal nearest RHS 157D; abaxial calyx nearest RHS 138A with veins nearest RHS 137B;

Flowers: Bilabiate corolla with arcuate hooded upper lip and tri-lobed lower lip; corolla about 13.0 mm long, 5.0 mm tall and 3.5 mm wide fused into tube in the proximal 5.0 mm; clustered at verticils with up to 12 flowers per verticil;

Petals: Bilabiate corolla; upper hood petal and flattened side to side vertically, with emarginate apex and base fused with labium;

Hood (upper) petal: Minutely puberulent to glabrous abaxial, glabrous adaxial; about 11.0 mm long, 2.0 mm tall and 1.5 mm across;

Labium (lower) petal: Consisting of three lobes, two proximal lobes projecting outwardly, about 2.0 mm long and 1.0 mm wide at base with rounded apex; center lobe cupped, with rounded emarginate apex, erose margin; about 5.0 mm long, 2.0 mm deep and 5.0 mm wide if stretched, with a 1.5 mm apical notch at apex; center lobe slightly concaved upwards; total labium about 8.0 mm long, 3.5 mm wide at the widest portion across middle of central lobe and 3.0 mm tall;

Petal color: Abaxial hood nearest RHS NN155D and adaxial hood petal nearest RHS NN155D; lower labium petal proximal lobes abaxial nearest RHS NN155D, and adaxial nearest RHS NN155D and center lobe abaxial nearest RHS NN155D, and adaxial nearest RHS NN155D;

Androecium: Two, fused with labium, arcuate within hood petal except when triggered by pollinator;

*Filament.*—Glabrous, fused about 4.0 mm from base of labium petal; curved around inside of hood petal; about 2.5 mm long and less than 0.3 mm diameter with a 1.0 mm trip mechanism at base; color nearest RHS NN155D.

*Anther.*—Glabrous, oblong, about 1.5 mm long and 0.5 mm diameter; longitudinal, basifixed; color nearest RHS N187A.

*Pollen.*—Nearest RHS 13A.

Gynoecium: One, superior; arcuate around inside of hood petal;

*Style.*—About 12.0 mm long and about 0.3 mm diameter; color nearest RHS NN155D.

*Stigma.*—Bifurcate and arcuate in the terminal 1.5 mm; apex acute; color nearest RHS NN155D.

*Ovary.*—Superior; color nearest RHS N144A.

Fruit: Nutlet, one to four per flower; rounded, about 1.5 mm diameter; color nearest RHS 202A;

Calyx: Campanulate; consisting of five sepals, three upper and two lower; 6.5 mm long and 2.5 mm across at apex;

Sepals: Five; fused in basal 3.5 mm; lower set bifid in distal 2.5 mm, upper set trifid in distal 0.5 mm; tube about 6.5 mm long and 4.5 mm tall at mouth and 2.5 mm wide; glandular abaxial and glabrous adaxial;

Sepal color: Adaxial nearest blend between RHS 145C and RHS 146D, with veins nearest RHS 146B and distally nearest 146B; abaxial base nearest RHS 144A with veins and distal blushing of nearest RHS 138B;

Bracts: Each verticil subtended by two opposite ovate to deltoid bracts; apex typically acuminate; base truncate; margin crenate and ciliolate; coarsely wavy to bent downward toward apex; glabrous above and pubescent below; bract size up to 9.0 mm long and 7.0 mm wide, decreasing distally;

Bract color: Adaxial surface between RHS NN137C and RHS 137A; abaxial surface nearest RHS 147B;

Peduncles: Raceme; pubescent; quadrangular in cross section; about 18 per plant; strong; upright; to about 47.0 cm tall and 4.0 mm across at base; flowering in upper 15.0 cm and to about 7.0 cm across with branches; compound branches in lower two to four nodes, upright at 55 to 60 degrees above horizontal; branches to about 22.0 cm long and 3.0 mm across; average internode distance about 6.0 cm;

Peduncle color: Nearest RHS 146C;

Pedicels: Cylindrical; puberulent to glandular; about 0.5 mm long and 0.5 mm diameter; slightly upright to nearly horizontal at flower anthesis and with seed set;

Pedicel color: Nearest RHS 146C;

Disease and pest resistance: Resistant to diseases and pests beyond that common to *Salvia* has not been noted. Specific diseases have not been tested, but not commonly browsed by *Cervinea* or *Oryctolagus*.

Growth recommendations: Plants of *Salvia* 'White Profusion' perform best with adequate moisture and good drainage and are hardy from USDA zone 3 to 8.

It is claimed:

1. A new and distinct perennial *Salvia* plant named 'White Profusion' as herein described and illustrated.

* * * * *